United States Patent
Whitney et al.

(10) Patent No.: US 9,513,703 B2
(45) Date of Patent: Dec. 6, 2016

(54) GESTURE-BASED WAKING AND CONTROL SYSTEM FOR WEARABLE DEVICES

(71) Applicant: Intel Corporation, Santa Clara, CA (US)

(72) Inventors: Kofi C. Whitney, Hillsboro, OR (US);
Giuseppe Raffa, Portland, OR (US);
Mark R. Francis, Portland, OR (US);
Andy S. Idsinga, Portland, OR (US);
Gregory A. Peek, Northplains, OR (US)

(73) Assignee: Intel Corporation, Santa Clara, CA (US)

( * ) Notice: Subject to any disclaimer, the term of this patent is extended or adjusted under 35 U.S.C. 154(b) by 209 days.

(21) Appl. No.: 14/142,700

(22) Filed: Dec. 27, 2013

(65) Prior Publication Data
US 2015/0185837 A1    Jul. 2, 2015

(51) Int. Cl.
*G06F 3/01* (2006.01)
*G06F 3/0354* (2013.01)
*A61B 5/00* (2006.01)

(52) U.S. Cl.
CPC ............... *G06F 3/014* (2013.01); *A61B 5/681* (2013.01); *G06F 3/017* (2013.01); *G06F 3/03547* (2013.01)

(58) Field of Classification Search
CPC ...... G06F 3/014; G06F 3/017; G06F 3/03547; A61B 5/681
See application file for complete search history.

(56) References Cited

U.S. PATENT DOCUMENTS

| 8,228,292 B1* | 7/2012 | Ruiz | G06F 1/1626 345/156 |
| 8,775,844 B1* | 7/2014 | Peterson | G06F 1/3265 713/323 |
| 2010/0219943 A1* | 9/2010 | Vanska | G06F 1/163 340/407.1 |
| 2012/0016641 A1* | 1/2012 | Raffa | G06F 1/1694 703/2 |

(Continued)

FOREIGN PATENT DOCUMENTS

KR    10-2006-0102121    9/2006

OTHER PUBLICATIONS

Pengyu Hong et al., "Gesture Modeling and Recognition Using Finite State Machines", ,IEEE Conference on Face and Gesture Recognition, Mar. 2000, 6 pages.

(Continued)

*Primary Examiner* — Ryan A Lubit
(74) *Attorney, Agent, or Firm* — Blakely, Sokoloff, Taylor & Zafman LLP

(57) ABSTRACT

A gesture-based waking and control system to wake a smartwatch device from a low-power state is described. In one embodiment, the system utilizes a pressure or proximity based wake gesture that is interpretable by low-power sensors. An embodiment of the system can be integrated within a wearable device, such as a smartwatch accessory that can be paired with a mobile electronic device, such as a smartphone. In one embodiment, the wearable device includes a set of low-power sensors that are to detect the wake gesture. In one embodiment, the wake gesture causes the device to enable an additional set of sensors and sensor processing logic to detect more advanced commands or gestures. In one embodiment, the wake gesture enables a display of the wearable device.

27 Claims, 8 Drawing Sheets

(56) References Cited

U.S. PATENT DOCUMENTS

| | | | |
|---|---|---|---|
| 2012/0071149 A1* | 3/2012 | Bandyopadhyay | G06F 1/1643 455/418 |
| 2012/0095352 A1 | 4/2012 | Tran | |
| 2012/0194976 A1 | 8/2012 | Golko et al. | |
| 2013/0072765 A1 | 3/2013 | Kahn et al. | |
| 2013/0163390 A1 | 6/2013 | Gossweiler, III et al. | |
| 2013/0176265 A1* | 7/2013 | Zurek | G06F 1/3262 345/174 |
| 2014/0118257 A1* | 5/2014 | Baldwin | G06F 3/017 345/158 |
| 2014/0156269 A1* | 6/2014 | Lee | G06F 1/3206 704/231 |

OTHER PUBLICATIONS

"Force Sensing Resistor Integration Guide and Evaluation Parts Catalog", 400 Series Evaluation Parts with Suggested Electrical Interfaces, State-of-the-Art Pointing Solutions for the OEM, Interlink Electronics, http://www.Interlinkelectronics.com, Version 1.0, Jun. 9, 2010, 26 pages.

Samsung, "SM-V700, User Manual", www.samsung.com, Oct. 2013.Rev.1.1, Oct. 2013, 53 pages.

Scott Steffes, "Modern Approaches to Gesture Recognition", Dec. 1, 2012, 40 pages.

"Projected capacitive touch panels designed for marine application", http://www.ecnmag.com/articles/2013/10/projected-capacitive-touch-panels-designed-marine-application, Oct. 16, 2013, 13 pages.

Jie Yang, "Hidden Markov Model for Gesture Recognition", CMU-RI-TR-94-10, The Robotics Institute, Carnegie Mellon University, May 1994, 31 pages.

PCT/US2014/068441, Notification of Transmittal of the International Search Report and the Written Opinion of the International Searching Authority, or the Declaration mailed Mar. 20, 2015, pp. 12.

* cited by examiner

GESTURE-BASED WAKING AND CONTROL SYSTEM FOR WEARABLE DEVICES

FIELD

Embodiments are generally related to wearable electronic devices, and more particularly to gestures for wearable electronic devices.

COPYRIGHT NOTICE/PERMISSION

Portions of the disclosure of this patent document contain material that is subject to copyright protection. The copyright owner has no objection to the reproduction by anyone of the patent document or the patent disclosure as it appears in the Patent and Trademark Office patent file or records, but otherwise reserves all copyright rights whatsoever. The copyright notice applies to all data as described below, and in the accompanying drawings hereto, as well as to any software described below: Copyright © 2013, Intel Corporation, All Rights Reserved.

BACKGROUND

Wearable mobile devices, such as smartwatch devices, are designed to provide the wearer ready access to information. Accordingly, wearable device users desire the ability to quickly and easily read information from the device, as well as a convenient mechanism to provide command input to the wearable device. Sensor-based gestures are one method of enabling wearable device functionality. However, the various devices and controllers used to enable sensor-based gestures consume power, and increase the overall power requirement of the wearable device. Accordingly, extensive use of sensors for gesture-based input can reduce the overall battery life of the device.

In some smart-watch wearable devices known in the art, sensors are placed in a low power state to reduce power draw. However, when the device's sensors are in a low power state, the device may not be able to wake the sensors in time to recognize incoming gestures, and may require additional interaction (e.g., hardware buttons) to wake the device. An alternative solution to a hardware button is increasing sensor wakeup sensitivity to avoid missed input. However, increasing the wake sensitivity of the sensors may result in a gesture detection system that is overly sensitive and prone to false positives, which in turn result in spurious sensor wake events that further deplete the device battery.

BRIEF DESCRIPTION OF THE DRAWINGS

The following description includes discussion of figures having illustrations given by way of example of implementations of the various embodiments. The drawings should be understood by way of example, and not by way of limitation. As used herein, references to one or more "embodiments" are to be understood as describing a particular feature, structure, or characteristic included in at least one implementation. Thus, phrases such as "in one embodiment" or "in an alternate embodiment" appearing herein, each describe various embodiments and implementation, and do not necessarily all refer to the same embodiment. However, they are also not necessarily mutually exclusive.

An overview of embodiments is provided below, followed by a more detailed description with reference to the figures.

DETAILED DESCRIPTION

A gesture-based waking and control system to wake a smartwatch device from a low-power state is described. The system provides support for discreet gestures and interactions that are less prone to false positives and provides improved power management capability for higher power sensors. The gesture-based waking and control system utilizes a wake gesture in the form of a "nudge" that is detectable by low-power sensors and interpretable by simple sensor logic. An embodiment of the system can be integrated within a wearable device, such as a smartwatch accessory that can be paired with a mobile electronic device, such as a smartphone. The wearable device includes a set of low-power sensors that are used to detect the wake gesture. In one embodiment, the wake gesture causes the device to enable an additional set of sensors and sensor processing logic to detect more advanced commands or gestures. In one embodiment, the wake gesture enables a display of the wearable device.

Figure 1A:
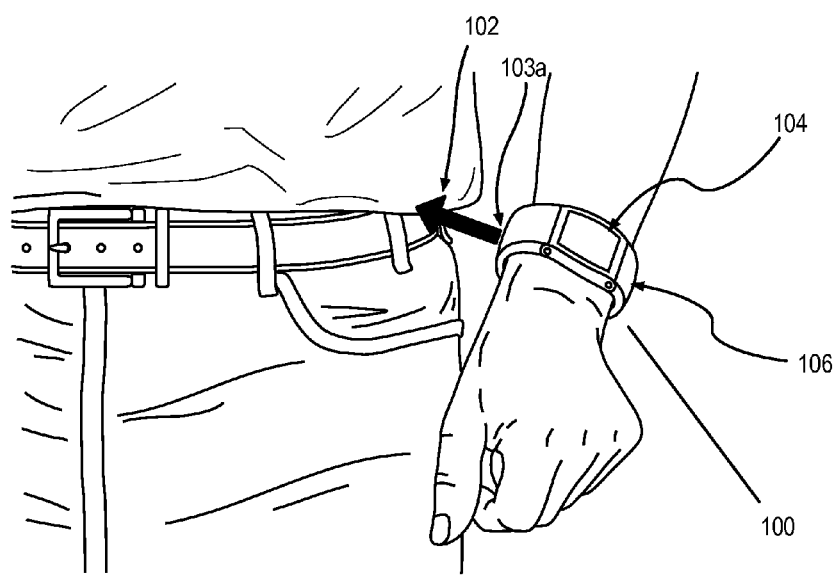
FIG. 1A is an illustration of an embodiment of a smartwatch wearable device in a start position of a nudge gesture.
Figure 1B:
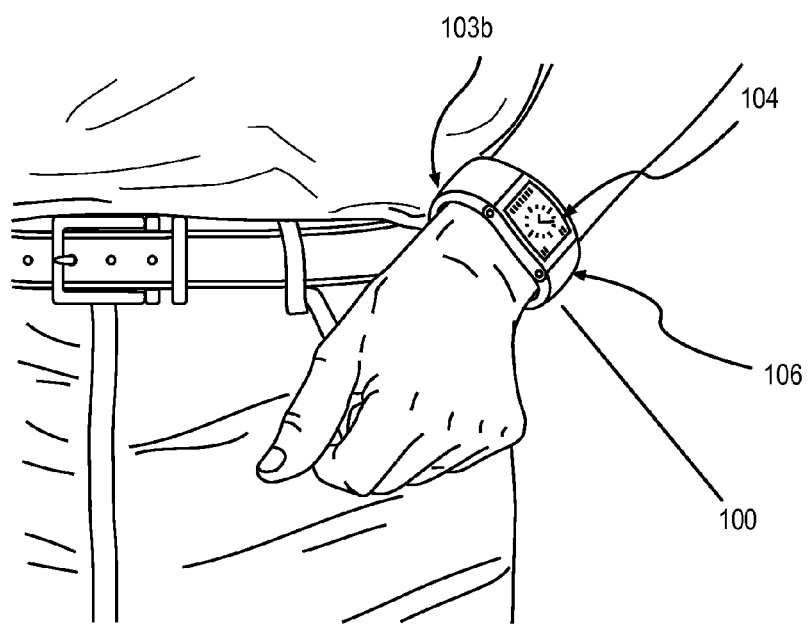
FIG. 1B is an illustration of an embodiment of a smartwatch wearable device in an end position of a nudge gesture.

FIGS. 1A-1B are illustrations of a smartwatch wearable device receiving a nudge gesture, according to an embodiment. The nudge gesture can be performed to initiate a wake event in the smartwatch device. In one embodiment, the wearer executes a nudge by pressing the smart watch against the wearer's body or a nearby surface. The wearer can perform the nudge gesture using only the wrist to which the device is attached, allowing a discreet interaction that is simple for sensor logic to recognize, and thus less prone to false positives.

FIG. 1A is an illustration of an embodiment of the smartwatch device 100 in a start position 103a of a nudge gesture. As illustrated, the device 100 includes a display region 104 to display information to a wearer of the device, and a band, bracelet, or other wrist attachment means 106 for attaching the wearable device to the wearer. The device 100 illustrated in FIG. 1A is in a sleep mode, in which the display 104, and a plurality of sub-systems of the device are in a low power state. The exemplary nudge gesture is used to wake the device 100 and causes the device to enter a ready state.

In one embodiment, the nudge gesture begins at a start position 103a, in which the smartwatch device 100 is held a distance away from the body of the wearer. The device 100 subsequently is moved from a gesture start position 103a along a first gesture path 102 towards the wearer's body and subsequently pressed against the wearer's body for a period of time. The precise distance traversed in the first direction 102 varies between embodiments. In one embodiment, the specifics of the gesture start position are discarded, and only the end position of the gesture is relevant for triggering the wake event. In one embodiment, a default set of nudge gestures is pre-determined. In one embodiment, the specifics of the nudge gesture are trainable and user configurable. For example, the nudge gesture can be configured to trigger in response to a detected pressure that continuously exceeds a threshold amount for greater than a period of time.

FIG. 1B is an illustration of an embodiment of the smartwatch device 100 in an end position 103b of the nudge gesture. In one embodiment, the end position 103b includes pressing the device against the wearer's body, or some other sufficiently solid surface. In one embodiment, the end position 103b is held for at least a period of time before the gesture is triggered. A low-power sensor, such as a pressure sensor, proximity sensor, or light sensor is embedded in the wrist attachment 106 of the smartwatch 100, to detect a nudge wake gesture.

In one embodiment, the nudge wake gesture causes an increase in pressure on the wrist attachment 106 that is detected by the pressure sensor. The pressure sensor triggers an electrical signal that is interpreted by a sensor controller within the smartwatch device 100, which determines if the data indicates the occurrence of a wake gesture. In one embodiment, the nudge wake gesture causes a proximity sensor to detect the close proximity of a surface, such as a portion of the wearer's body. The proximity sensor outputs data to sensor logic that interprets the sensor data, to determine if the data indicates the occurrence of a wake gesture. In one embodiment, the nudge wake gesture causes an ambient light sensor to detect a drop in ambient light at a device surface. For example, if a portion of the device is occluded, such as when the wrist attachment 106 is pressed against a portion of the wearer's body, an ambient light sensor on the portion will detect a reduction in light at the sensor. The light sensor data is then interpreted by sensor logic, alone or in conjunction with other sensor data, to determine if the collected data indicates the occurrence of a wake gesture.

In one embodiment, when a wake gesture is detected, sensor-processing logic signal powers management logic to indicate that a wake gesture has been received. The wake gesture triggers the power management module to enable one or more of the multiple sub-components of the device. The specific sub-components enabled vary by embodiment. In the exemplary illustration of FIG. 1B, the display 104 of the smartwatch device 100 is enabled in response to the nudge gesture, and is able to display information to the wearer. In one embodiment, the display is not immediately enabled in response to the wake gesture. Instead, an additional set of sensors is enabled in the device 100, including higher power sensors that are otherwise held in a low-power state to reduce the operational power requirements of the device 100.

Once enabled, the additional sensors are used to accept input commands, such as voice commands, motion gestures, touch gestures, or multi-modal gestures involving multiple types of sensors. In one embodiment, the additional sensors include motion sensors to detect motion gestures. Additionally, an infrared or proximity sensor can be used to determine if one of the smartwatch displays is within the line of sight of a wearer, or to determine if a wearer is looking directly at the display. For example, the motion sensors can detect an arm or wrist twisting gesture, and the wearer can configure a gesture to enable one or more displays 104 of the device 100 in response to the gesture. The additional infrared or proximity sensors are then used to allow the wearer to configure a wrist gesture that is triggered only if the wearer is also looking at a display of the device.

Figure 2:
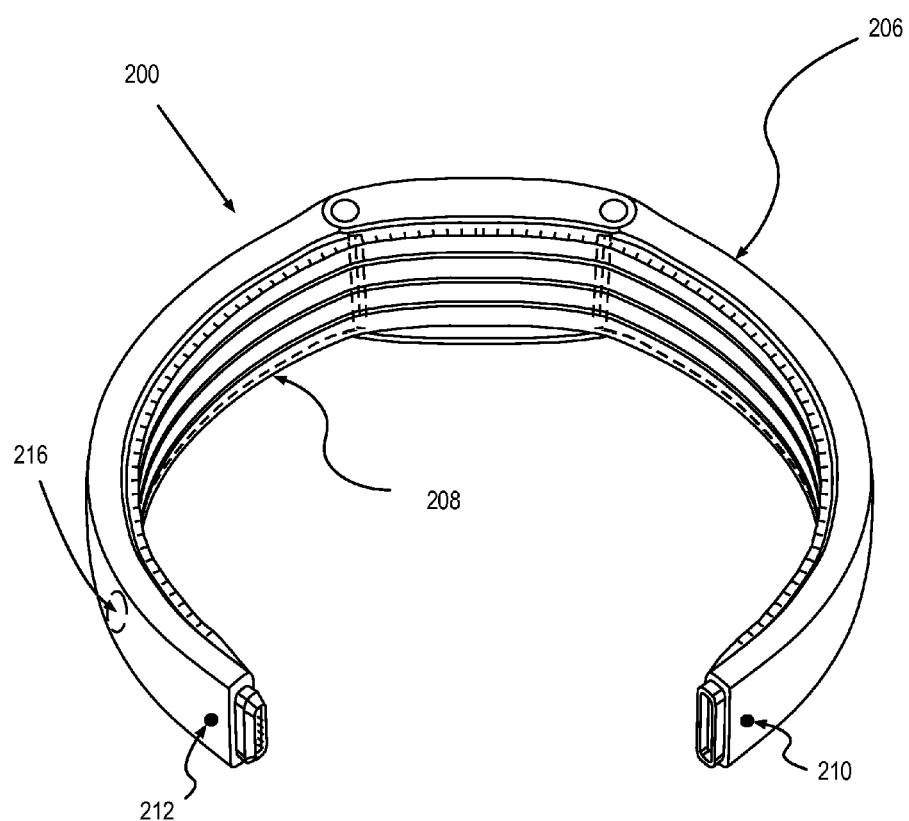
FIG. 2 is an illustration of sensor integration for a wearable device, according to an embodiment.

FIG. 2 is an illustration of sensor integration for a smartwatch wearable device, according to an embodiment. The wearable device 200 represents an embodiment of the smartwatch device 100 of FIG. 1. However, some aspects have application to wearable devices in general. In one embodiment, the wearable device 200 includes an attachment mechanism 206 having multiple sensors, including a pressure sensor 208 having one or more pressure or force sensing elements. As illustrated, the pressure sensor 208 layers the inner surface of the wrist attachment 206, to detect pressure against the inner surface of the attachment during the nudge gesture. In one embodiment, the pressure sensor 208 is embedded internally within the attachment mechanism 206 to detect compressive forces between the outer surfaces of the attachment. In one embodiment, the outer surface of the attachment 206 includes pressure-sensing elements to detect pressure against the outer surface of the wrist attachment 206.

The pressure sensor includes force-sensitive elements, such as a piezoelectric sensor or one or more force-sensitive resistors. When force is applied to the force-sensitive elements of the pressure sensor, the resistance of the sensor elements decreases, causing an increase in conductance within the sensor, and an increase in an output voltage of the sensor element. When sensor logic detects the increased voltage output of the pressure sensors caused due to the occurrence of a nudge gesture, the logic requests a power management module to wake one or more sub-components of the smartwatch device. In one embodiment, various types nudge gestures are configurable to be registered at a various user configurable force or pressure thresholds, according to the wearer's preferences.

In one embodiment, the set and complexity of available nudge wake gestures is limited in order to simplify the complexity of the logic required to detect the sensors. In one embodiment, additional sensors and sensor logic is included in the device 200 to enable a wider array of nudge gestures, including more complicated or multi-modal gestures that are used to wake the device or to provide command input. A low-power proximity sensor 214 can be used to detect nudges by detecting the proximity of the sensor 212 to a surface. Additionally, an ambient light sensor 210 can be used to detect changes in ambient light when the surface of the wearable device 200 is pressed against the body.

In one embodiment, a touch sensitive region 216 of the wrist attachment 206 is able to detect touch-based gesture input, in addition to any touch input received from a touch screen of the device. The touch sensitive region 216 can be a used to improve the vocabulary of gestures available for various tasks, and individual touch gestures can be configured based on the touch response detected at one or more touch sensitive regions of the wearable device 200. Additional sensor processing logic coupled to the additional sensors can be trained to enable gesture recognition via a dedicated gesture recognition system. For example, the area of pressure can be identified from an array of sensors and a machine-learning algorithm can be trained to recognize the gesture based on the properties of a gesture (e.g. time, pattern/frequency, pressure). In one embodiment, the sensor logic processes touch data in addition pressure, proximity and light data. For example, a capacitive touch sensor in the touch sensitive region 216 can complement the pressure sensor, to enable gestures that, for example, require skin contact as a component of the gesture.

Figure 3:
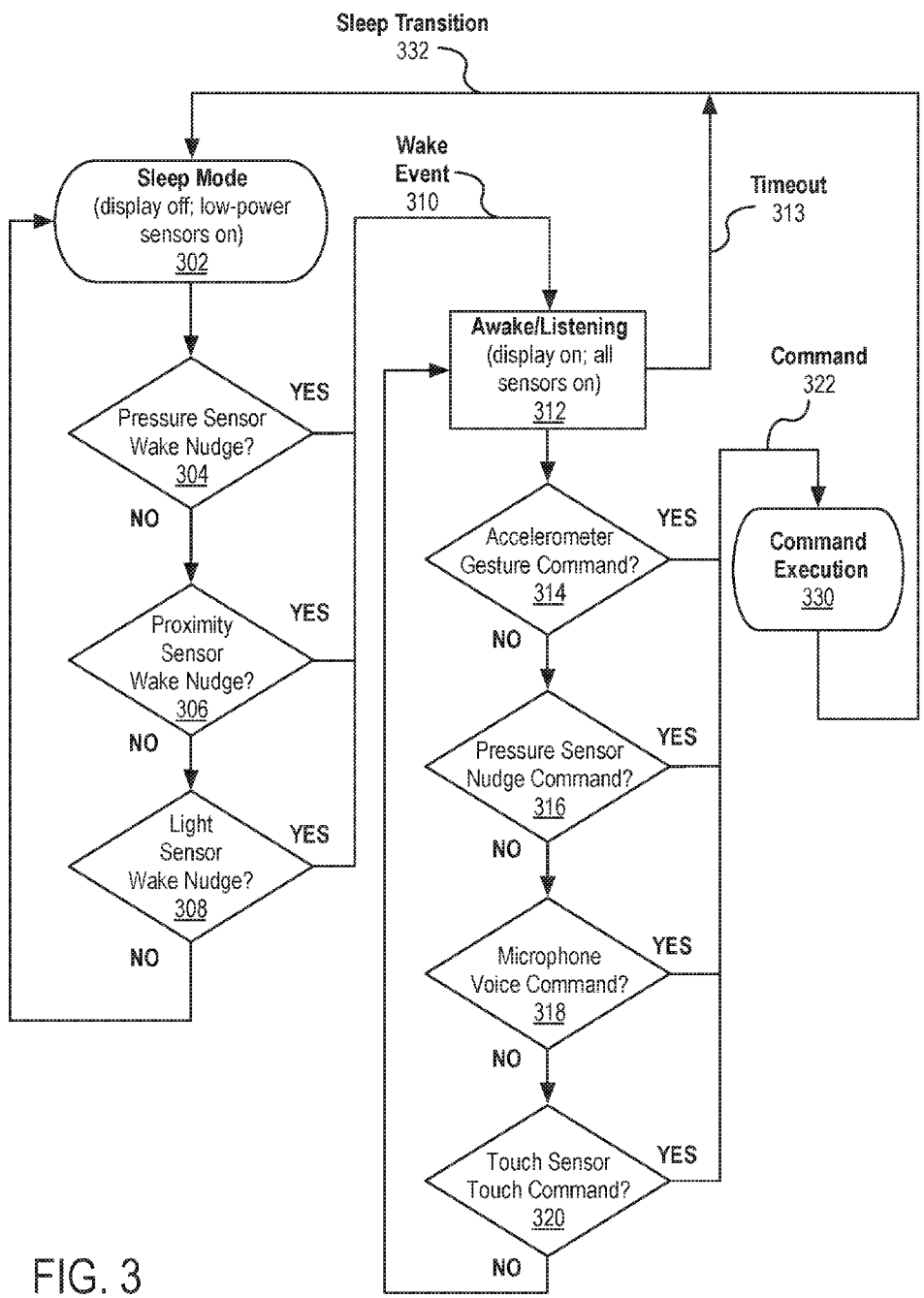
FIG. 3 is a flow diagram of a method of waking subsystems in a wearable device, according to an embodiment.

FIG. 3 is a flow diagram of a method of waking subsystems in a wearable device, according to an embodiment. In one embodiment, when the wearable device is in a low power sleep mode, as shown at 302, multiple sub-systems of the device are disabled, or in a low power state. For example, the display device and display subsystem are disabled to reduce power consumption. Higher power sensors in the device are also disabled to further reduce device power consumption. In one embodiment processing logic of the device, including the central processor and sensor processing logic is in a low power idle or sleep state. In one embodiment, low-power sensor processing logic is available during the sleep state to interpret a simplified set of gestures.

The wearable device transitions from sleep mode at 302 via a wake gesture detected from signals transmitted by a low-power sensor (e.g., pressure, proximity or light sensors). In one embodiment, a smartwatch wrist wearable device includes one or more pressure sensors or pressure sensor elements located within a watchband, bracelet or other mechanism that is used to attach the device to a user's wrist. In one embodiment, the smartwatch includes one or more proximity sensors at one or more locations of the smartwatch. In one embodiment, the device also includes one or more light sensors. Each sensor transmits signals that can be interpreted by sensor processing logic as a nudge wake gesture.

As shown at 304, a pressure sensor, such as a piezoelectric sensor or a force sensitive resistor, can output a signal indicating a change in pressure at the pressure sensor resulting from the performance of a wake nudge. The signal is interpreted by the sensor logic to determine if the signal corresponds to a nudge wake gesture. If a wake gesture is recognized by the sensor logic, a wake event 310 is sent to a power management controller, or other power management logic, to cause the device to enter an awake/listening mode, as shown at 312.

The wearable device can also include one or more proximity sensors as an alternate or additional sensing mechanism to the pressure sensor. In one embodiment, a proximity sensor is used at 306 to detect an alternate nudge wake gesture based on a specific pattern of motion relative to portion of the user's body. In one embodiment, the proximity sensors are included in addition to the pressure sensor, to supplement the pressure sensor. Accordingly, the nudge wake gesture at 306 can be a multi-mode gesture that includes both a proximity component and a pressure component.

The wearable device can also include one or more light sensors as an alternate or supplemental sensing mechanism to the pressure sensor or the proximity sensor. In one embodiment, one or more light sensors are used at 308 to detect an alternate nudge wake gesture based on a change in ambient light detected at the smartwatch. For example, a nudge gesture can consist of an occlusion motion. In one embodiment, briefly covering, then uncovering the face of the smartwatch at 308 wakes the device from a low-power state. The sensor data collected by light sensors is used as correlating data with the pressure or proximity sensor, to reduce the instances of false positive detections of the wake gesture. If the sensor logic determines that the sensor data collected by one or more of either the pressure sensor at 304, the proximity sensor at 306, and the light sensor at 308 does not correspond to a nudge wake gesture, the device remains in sleep mode at 302. Once a wake gesture is detected, a wake event 310 causes the device to transition into an awake/listening mode at 312.

In one embodiment, the awake/listening mode at 312 is a fully awake mode in which the display device and display subsystems are enabled to display information to a user, and higher power consuming sensor devices are enabled to detect input of a command from the device wearer, such as an additional gesture, or a voice command. For example, sensor logic can continually process incoming sensor data to detect one or more of an accelerometer based gesture command at 314, a more complex nudge pressure pattern corresponding to a nudge command at 316, an incoming voice command detected by a microphone at 318, or a touch sensor command at 320. When sensor logic detects one or more incoming commands via one or more sensor modes, the command 324 is transmitted to one or more central or application processors for execution at 330. As shown at 313, if a command is not detected after a configurable period of time, the system may time out of the awake/listening mode, and transition back into the sleep mode at 302 via the sleep transition shown at 332. Additionally, after executing a command the wearable device can return to the sleep mode via the sleep transition shown at 332.

In one embodiment, the awake/listening mode at 312 is a listening mode in which the display is not immediately disabled, and a subset of the available sensors and sensor logic are enabled to listen for additional input. In one embodiment, a subset of the additional sensors and sensor logic is enabled and used to verify that the wake gesture is a legitimate wake gesture, rather than a false positive. For example, the display device can remain in a low power state until an additional sensor, such as a proximity or infrared sensor, detects that the wearer is looking at the display device. In one embodiment, additional sensors are enabled during the wake gesture to gather additional sensor input to validate the wake gesture. For example, when pressure sensor data is received that corresponds to the beginning of a wake gesture, additional sensors including a proximity sensor, a light sensor, or a touch sensor can activate and begin to gather sensor data. If the additional sensor data corresponds to expected sensor input during a wake gesture, the device can enter a fully awake mode, to accept commands.

In one embodiment, the sensors are activated according to a wakeup chain, such that increasingly more complex sensors with higher power consumption and processing logic requirements are enabled to gather data before the device transitions until a fully awake state. For example, a pressure sensor, light sensor, or proximity sensor can detect the beginning of a wake gesture, which enables a touch sensor or microphone to accept input, and the sequential combination of the low power sensor activity and the higher power sensor activity causes the device to enter an awakened state.

In one embodiment, a simple set of nudge gestures is detected by low power sensor logic, and once a wake nudge is detected, more advanced sensor logic, including multi-modal sensor logic, is enabled to recognize command gestures from multiple sensors. In one embodiment, piezoelectric or capacitive sensors are included to gather gesture data, which improve gesture detection accuracy and enables a wider vocabulary of gestures for various tasks. For example, individual touch gestures can be recognized based on the response of the smartwatch material, or pressure gestures can be combined with touchscreen input. The touch sensor data, a touch intensity map, centroid coordinates, and direction of the centroid's movement can be utilized to train the sensor processor logic with a gesture recognition system (e.g., Finite State Machine (FSM), Hidden Markov Model (HMM), Dynamic Time Warping (DTW), etc.). In one embodiment, the sensor processing logic is trained to detect a pattern of sensor data that corresponds with an intentional user gesture, and disregards random, unintentional input that may be detected by the sensors. This allows the sensor logic to determine if an actual gesture occurred, or if the sensor input data pattern is a false positive. For example, sensor data that indicates a momentary hard bump against a surface may indicate a false positive. In one embodiment, sensor logic discards data that does not indicate that a gesture end position is held for at least a period of time.

Multiple combinations of sensors can be used for multi-mode gesture recognition. In one embodiment, the trained sensor logic analyzes data from pressure, proximity, and light sensors to recognize a nudge wake gesture. In one embodiment, the sensor logic is trained to recognize touch sensor data in addition to pressure sensor data, to enable a more advanced gesture vocabulary, and to improve the accuracy of the gesture recognition. For example, a profile of the touch sensor data can be used to determine the type of nudge (e.g., wake nudge, command nudge) and to filter false positives. In one embodiment, touch sensor data is combined with voice input, such that the device wakes in conjunction with a pressure gesture and a voice command.

Figure 4:
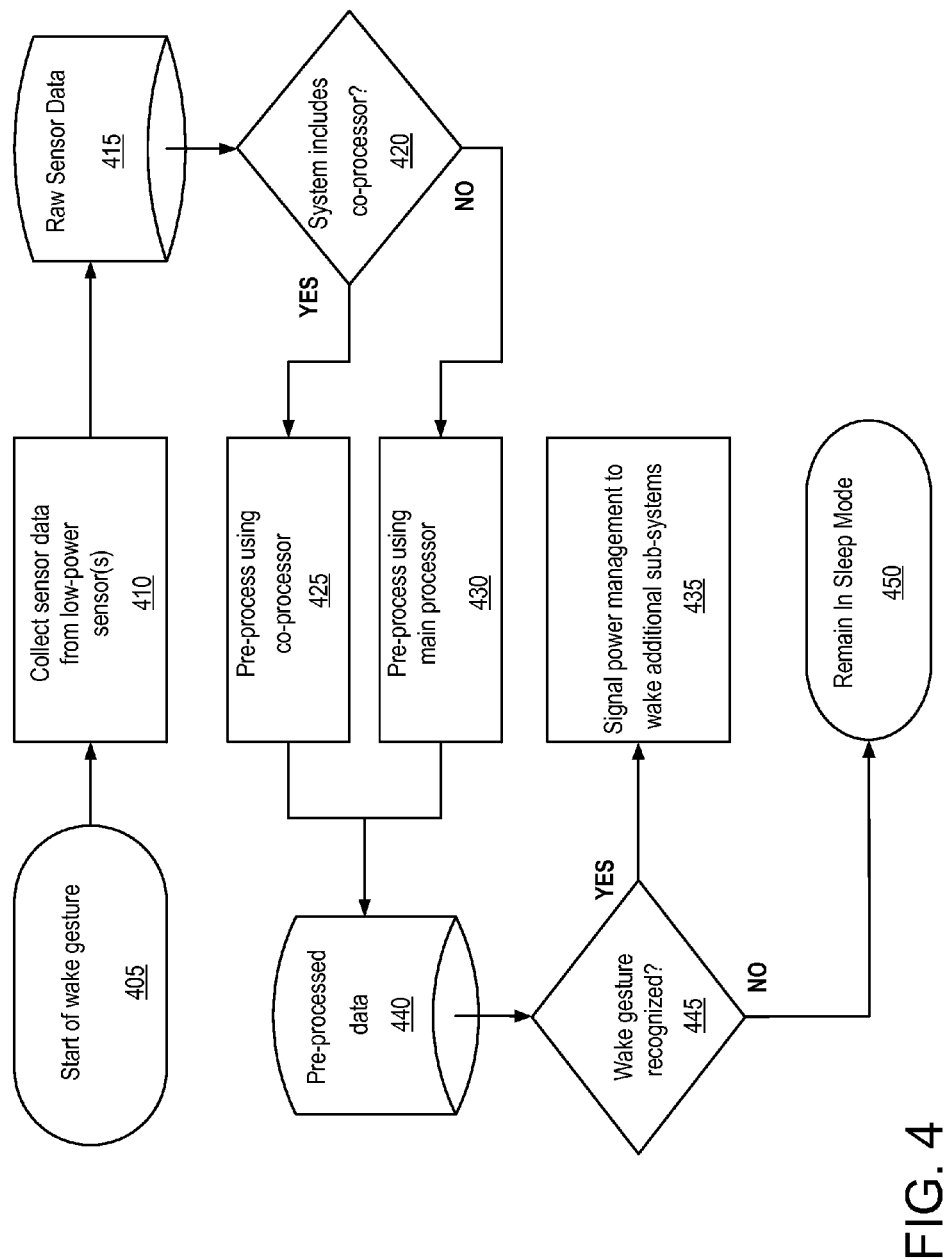
FIG. 4 is an illustration of a method of processing sensor data in a wearable device, according to an embodiment.

FIG. 4 is an illustration of a method of processing sensor data in a wearable device, according to an embodiment. In the illustration, block 405 indicates the start of a wake gesture, such as a nudge gesture detected via a low-power sensor (e.g., pressure, proximity, light). In one embodiment a smartwatch wearable device includes a pressure sensor array in the watchband or bracelet of the smartwatch. The pressure sensor array can include multiple sensor elements that begin outputting a particular sensor data pattern when a user begins a nudge gesture to wake the smartwatch device. In response to the start of the wake gesture, the device begins to collect sensor data generated by one or more sensors at 410. The collection includes the pressure sensors, and can also include other low-power sensors that collect data for gesture data verification or correlation. The collection results in a set of raw data for preprocessing, which is shown at 415.

In one embodiment the smartwatch device includes one or more co-processors, or other logic for performing sensor processing or pre-processing. If the smartwatch includes a co-processor, as determined at 420, then preprocessing may be accomplished utilizing the co-processor, as shown at 425. Otherwise, the preprocessing is accomplished utilizing a main system or application processor of the wearable device, as shown at 430. In each case, a set of pre-processed data 440 is stored for further processing by a gesture recognition module using one or more sensor recognition algorithms. If the gesture recognition module recognizes a wake gesture at 445, the module signals a power management module to wake the additional subsystems (e.g., additional sensors, display devices, etc.) as shown at 435.

The gesture recognition module may fail to recognize the wake gesture for various reasons. For example, the gesture may have been incomplete, or may not have been completed before a timeout period. The gesture may have been complete, but differed from the default or user-configured gesture that is designated as one of the possible wake gestures. Additionally, in one embodiment sensor data is collected from multiple types of sensors to reduce the incidence of false positives, and false positive detection can reject an otherwise detected gesture, flagging the gesture as unrecognized. If the gesture recognition module does not recognize a wake gesture at 445, the device remains in sleep mode, as indicated at 450.

Figure 5:
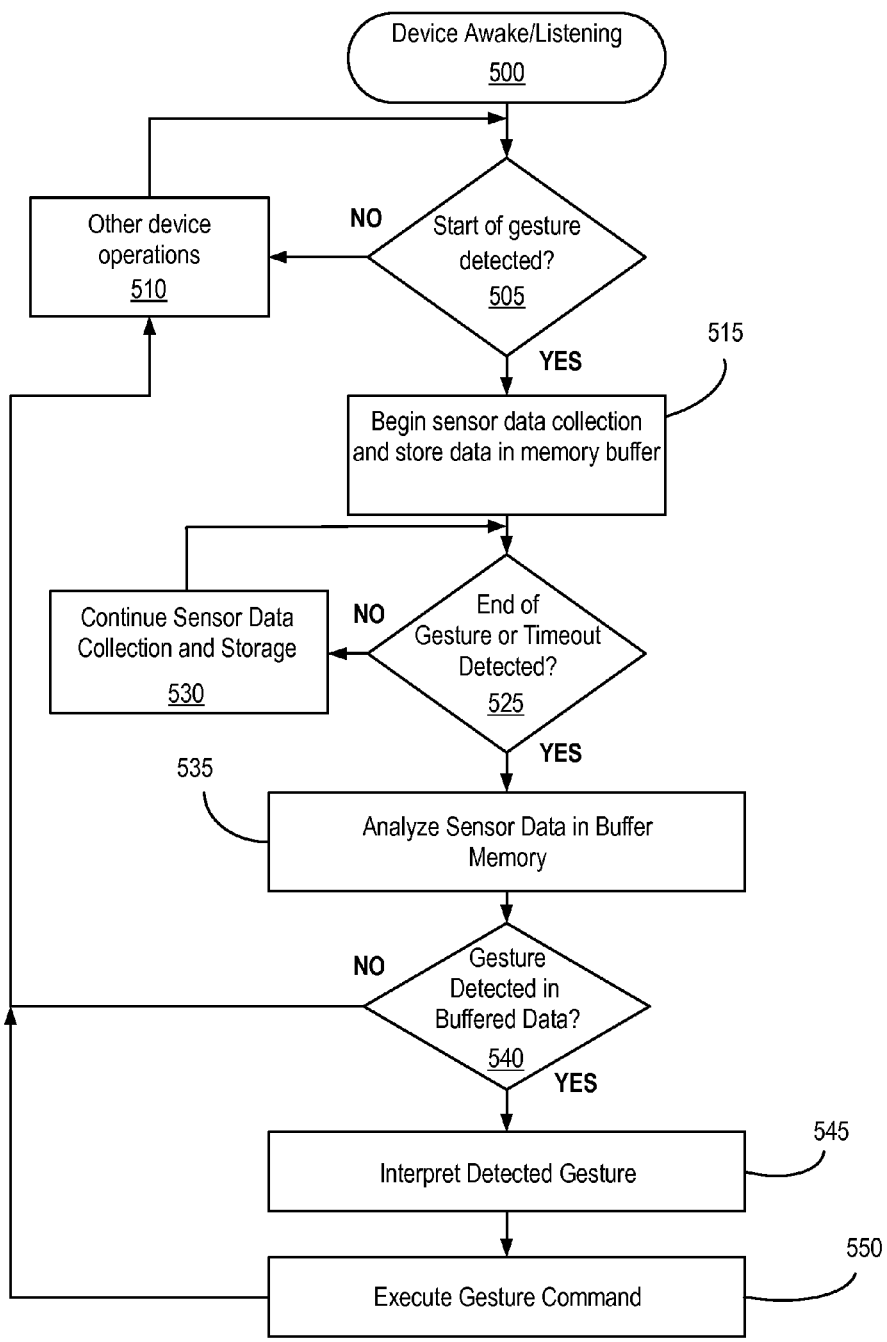
FIG. 5 is an illustration of a process for collecting and interpreting gesture data, according to an embodiment.

FIG. 5 is an illustration of a process for collecting and interpreting gesture data, according to an embodiment. After receiving a wake gesture an embodiment of a wearable device enters an awake/listening mode. As illustrated at block 500, during the awake/listening mode the wearable device is configured to detect the start of a command gesture, as shown at 505. The gesture can include data from any of the sensor devices enabled on the device, including low power sensors (e.g., pressure sensors) and higher power sensors (e.g., accelerometers). Until the start of a gesture event is detected the wearable device can continue with other device operations at 510. This includes circumstances in which the wearable device receives sensor data from one or more sensor devices, where the incoming data does not match a pattern indicating the start of a gesture.

When the start of the gesture is detected, the wearable device initiates the collection of sensor data generated by the sensor elements of the wearable device, as shown at 515. The collected sensor data is stored in a buffer for access after the end of the gesture. As shown at 525, the wearable device collects sensor data until an end of the gesture is detected, or a timeout period occurs. The existence and length of a time out period varies between the type of command and the type of gesture. Until the end of gesture or timeout is detected, the mobile device is to continue to collect and store sensor data, as shown at 530. Upon detecting the end of a gesture event, or a timeout of the collection of gesture data, a gesture recognition module analyzes the sensor data stored in the sensor data buffer, as shown at 535. If the sensor data pattern is not detected in buffered data at 540, the wearable device continues with other operations 510. If sensor data corresponding to a gesture is detected, a gesture recognition module interprets the collected sensor data at 545 to identify the gesture. The wearable device then executes a command intended by the gesture, as shown at 550, before returning to other operations at 510.

Figure 6:
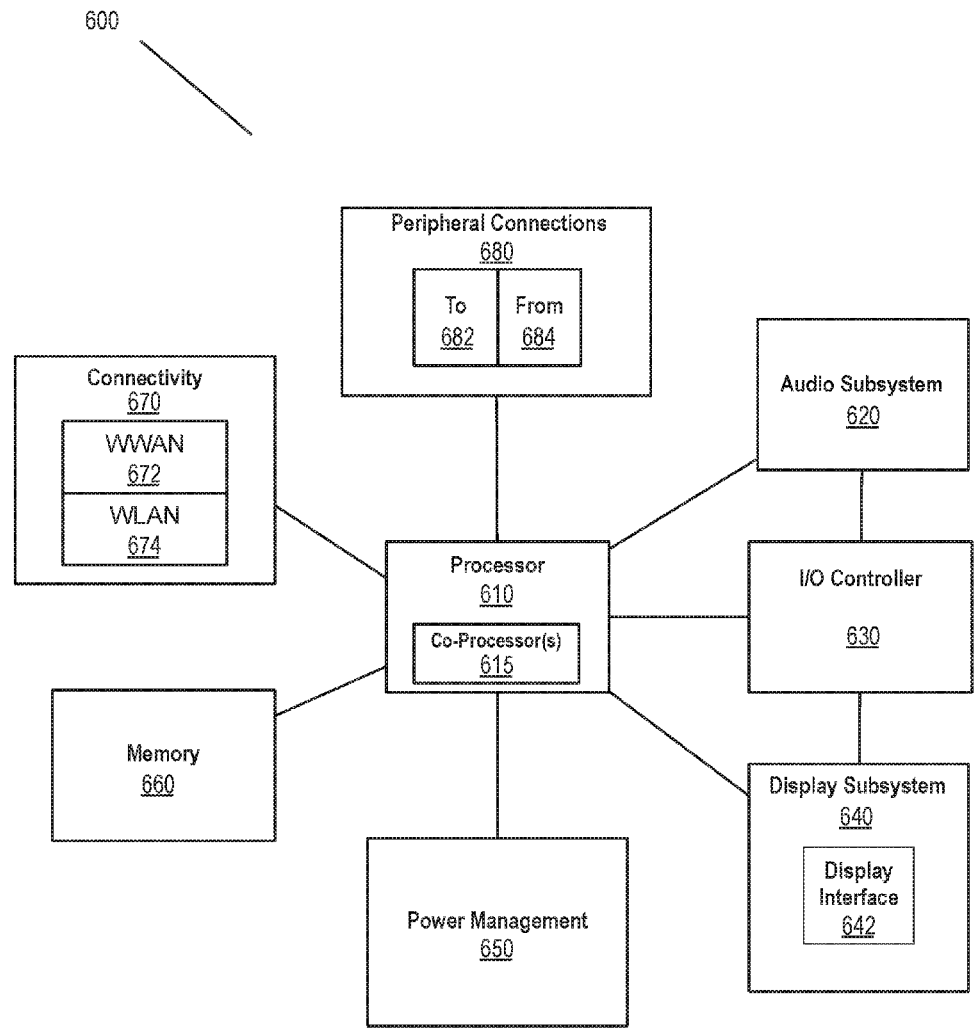
FIG. 6 is a block diagram of a wearable device in which an embodiment of gesture-based waking and control can be utilized.

FIG. 6 is a block diagram of a wearable device in which an embodiment of gesture-based waking and control can be utilized. Device 600 represents a wearable computing device, such as a smartwatch, or smart wristwatch device. It will be understood that certain of the components are shown generally, and not all components of such a device are shown in the device 600, and other device configurations are within the spirit of the embodiments. The device 600 includes processor 610, which performs the primary processing operations of the device 600. The processor 610 can include one or more processing devices, such as specialized microprocessors, general-purpose application processors, microcontrollers, programmable logic devices, or other processing elements.

The processing operations include the execution of an operating platform or operating system on which device functions are executed. The processing operations also include operations related to I/O (input/output), operations related to power management, and operations related to connecting the wearable device 600 to another device. The processing operations can also include operations related to audio I/O and/or display I/O. In one embodiment, one or more co-processors 615 are available for additional processing operations. The co-processors 615 can perform pre-processing of raw sensor data to transform data into a more easily handled format. Pre-processing operations can include data normalization, time tagging to correlate data measurements with event times, and the imposition of a smoothing filter to smooth abrupt changes in values. In one embodiment, a controlling integrated circuit for processing or pre-processing sensor input interfaces with the sensors, to provide pre-processed sensor data to the processor 610 or co-processor 615. In one embodiment, sensor data passes through multiple sensor controllers and co-processors before the sensor data reaches the processor that is responsible for handling input for all sensors.

In one embodiment, the wearable device 600 includes an audio subsystem 620, which represents hardware (e.g., audio hardware and audio circuits) and software (e.g., drivers, codecs) components associated with providing audio functions to the computing device. Audio functions include speaker output and microphone input. Audio output can also be performed via a lineout connector or a wireless audio-output. Devices for such functions can be integrated into the wearable device 600, or connected to the device. In one embodiment, a user can interact with the wearable device 600 by providing audio commands once the device is placed in a listening mode via a nudge wake gesture.

An I/O controller 630 includes hardware devices and software components related to interactions between users, or additional devices that connect with the wearable device 600. The I/O controller 630 can use one or more of the peripheral connections 680, or wireless connectivity 670 to facilitate the connection with I/O devices. The I/O controller 630 can also interact with other device subsystems. For example, the I/O controller 630 interacts with the audio subsystem 620 to receive input or commands through a microphone coupled to the audio subsystem 620.

Additionally, the I/O controller 630 interacts with the display subsystem 640 to receive input from a touchscreen coupled to the display. In one embodiment, I/O controller 630 also assists in the management of the sensor devices described herein (e.g., pressure sensors, proximity sensors, light sensors, accelerometers, gyroscopes, etc.), or other sensor hardware that can be included in the wearable device 600. The input can be part of direct user interaction or for providing environmental input and context awareness to the system.

A display subsystem 640 includes hardware (e.g., display devices) and software (e.g., drivers) components that provide a visual and/or tactile display. The display subsystem 640 includes a display interface 642, which in turn includes a screen, or the particular hardware device used to provide a visual display. In one embodiment, the display interface 642 includes logic separate from processor 610, such as graphics processing logic, to perform at least some processing related to the display. The display subsystem 640 also includes a touchscreen device to accept input commands and gestures.

In one embodiment, the wearable device 600 includes a power management module 650 to manage battery power usage, battery charging, and power saving operations, such as enabling or disabling device subsystems, or placing sub-systems into a low power state. In one embodiment, the power management module 650 maintains a set of sensors in a normally low-power state, such that the sensors are disabled or inactive unless woken by a nudge gesture. The power management module maintains a different set of low-power sensors in a normally active state to detect a wake gesture.

A memory subsystem 660 of the wearable device 600 includes memory devices for storing information in the device, as well as memory to store instructions for execution by the processor 610 or one or more co-processors 615 of the device. The memory subsystem 660 includes nonvolatile (state does not change if power to the memory device is interrupted) and volatile (state is indeterminate if power to the memory device is interrupted) memory devices. Memory 660 can store application data, user data, music, photos, documents, or other data, as well as system data (whether long-term or temporary) related to the execution of the applications and functions of system 600.

Connectivity 670 includes hardware devices and software components to enable the wearable device 600 to wirelessly communicate with external devices such as other computing devices, wireless access points or base stations. Wireless communication refers to transfer of data through the use of modulated electromagnetic radiation through a non-solid medium. The connectivity 670 module supports multiple different types of wireless connectivity. To generalize, the wireless device 600 is illustrated with wireless wide area network (WWAN) connectivity 672, such as cellular connectivity and wireless local area networking (WLAN) connectivity 674. WWAN connectivity 672 refers generally to voice and data network connectivity provided by wireless carriers, such as provided via variations or derivatives of GSM (global system for mobile communications), CDMA (code division multiple access), LTE (long term evolution), or other mobile wireless standards. WLAN connectivity 674 refers to shorter-range wireless connectivity such as Bluetooth personal area networks (PAN), Wi-Fi, and near field communication (NFC).

Peripheral connections 680 include hardware interfaces and connectors, as well as software components (e.g., drivers, protocol stacks) to make peripheral connections, which can communicate wirelessly or, in one embodiment, via a wired connection. It will be understood that device 600 can be a peripheral device ("to" 682) to other computing devices, as well as have peripheral devices ("from" 684) connected to it. The wearable device 600 can have a "docking" connector to connect to other computing devices for purposes such as managing (e.g., downloading and/or uploading, changing, synchronizing) content. Additionally, a docking connector can allow the device to connect to certain peripherals that allow the wireless device 600 to control content output, for example, to audiovisual or other systems. The wireless device can make peripheral connections via proprietary connection hardware, or via standard hardware, such as Universal Serial Bus (USB) connector, DisplayPort including MiniDisplayPort (MDP), High Definition Multimedia Interface (HDMI), or other connection hardware.

Figure 7:
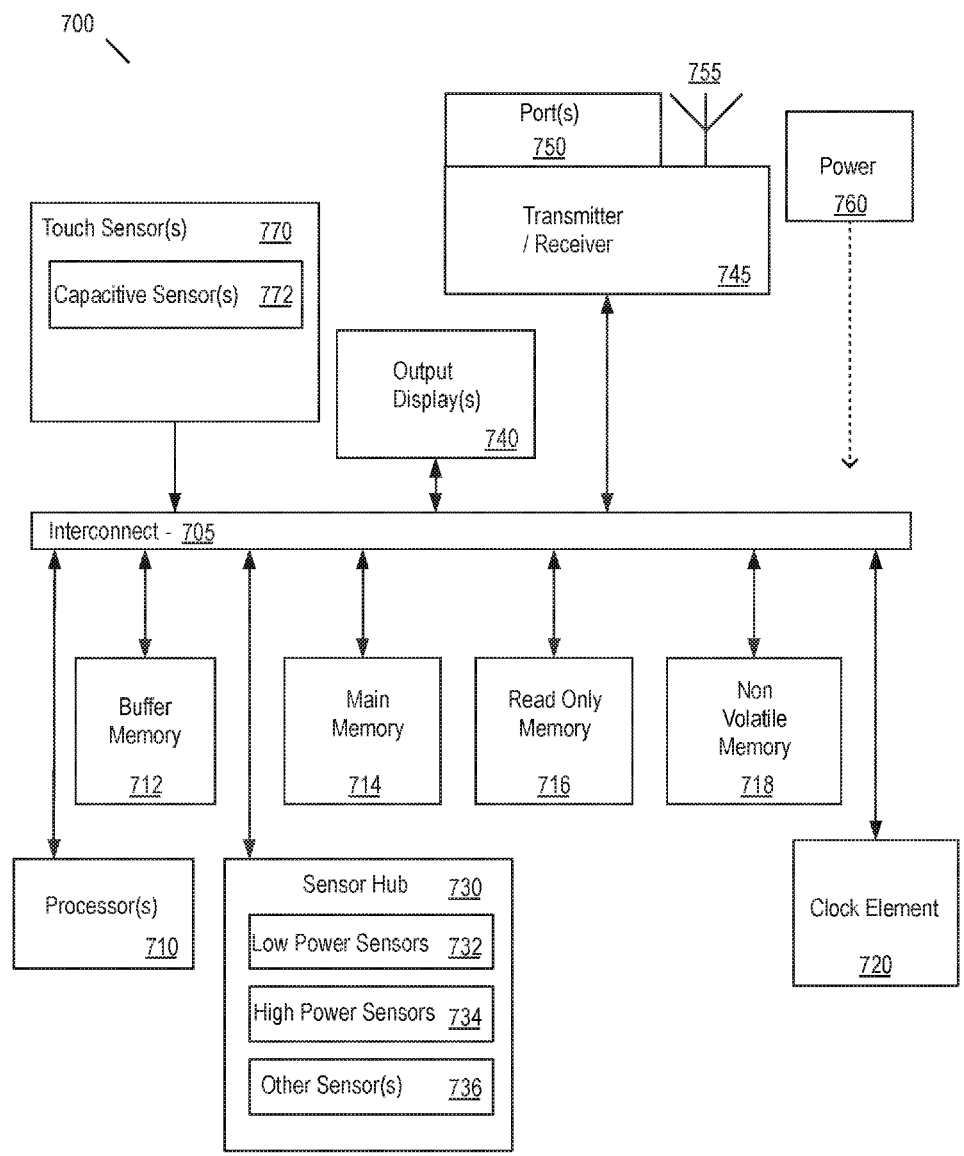
FIG. 7 is a block diagram of an additional device in which an embodiment of gesture-based waking and control is utilized.

FIG. 7 is a block diagram of an additional device in which an embodiment of gesture-based waking and control is utilized. The block diagram represents a wearable device as described herein, and also represents an additional wearable or mobile device which can couple with the wearable device of FIG. 6. In one embodiment, the device 700 comprises an interconnect crossbar 705 or other communication mechanisms for the transmission of data. The device 700 includes a processing means such as one or more processors 710 coupled with the interconnect 705 for processing information. The processors 710 comprise one or more physical processors cores, which can contain multiple logical processors. The interconnect 705 is illustrated as a single interconnect for simplicity, but may represent multiple different interconnects or buses and the component connections to such interconnects may vary. The interconnect 705 shown in FIG. 7 is an abstraction that represents any one or more separate physical buses, point-to-point connections, or both connected by appropriate bridges, adapters, or controllers.

In one embodiment, the device 700 includes a buffer memory 712 to store motion data. The buffer memory 712 can be coupled with, or integrated within the processors 710. The wearable device 700 includes a sensor hub 730, which includes a set of low power sensors 732 (e.g., pressure sensors), which are used to wake the wearable device from a sleep state, and a set of high power sensors 734 (e.g., motion sensors) that are enabled once the device enters a wake or operation state. In one embodiment, a set of other sensors 736 is available, which include sensors that can be used in conjunction with one of the low or high power sensors.

In one embodiment, the sensors store sensor data from the sensor elements 730 into the buffer 712 upon detection of a start of gesture, and ceases storage of such motion data upon the detection of the end of the gesture. In one embodiment, the wearable device 700 includes one or more touch sensors 770, including capacitive sensors 772, or other sensors, such as optical or proximity sensors that can be used as touch sensors. In one embodiment, a start of gesture data event or an end of gesture data event may include a gesture detected by contact with the one or more touch sensors, as described above.

The device 700 includes a random access memory (RAM) or other dynamic storage device or element as a main memory 714 for storing information and instructions to be executed by the processors 710. Random access memory includes dynamic random access memory (DRAM), which requires refreshing of memory contents, and static random access memory (SRAM), which does not require refreshing contents, but at increased cost. In one embodiment, the main memory 714 is coupled to the processor 710 over a low power memory bus, or is integrated within the processor 710. In one embodiment, memory of the system may include registers or other special purpose memory.

In one embodiment, the device 700 includes read only memory (ROM) 716 or another static storage device for storing static information and instructions for the processors 710. The device 700 also includes one or more non-volatile memory elements 718 for the storage of certain data. In one embodiment, the device includes a clock element or other time measurement element 720, where the clock element 720 includes the measurement of time in connection with the receipt and interpretation of motion sensor data, or when analyzing a pattern of pressure sensor data from an array of pressure or force sensing elements.

In one embodiment, the device 700 is coupled via the interconnect 705 to an output display 740. In one embodiment, the display 740 may include a liquid crystal display (LCD), an organic light emitting diode (OLED) or another display technology for displaying content to a user. The display 740 can also include a touch-screen that is utilized as at least a part of an input device. In one embodiment, the display 740 includes an integrated audio device, such as a speaker for providing audio information, or a microphone for receiving audio commands.

In one embodiment, one or more transmitters or receivers 745 are coupled to the interconnect 705, for coupling with or communicating with a network, or an additional display device. In one embodiment, the device 700 includes one or more ports 750 for the reception or transmission of data. The device 700 also includes one or more antennas 755 for the reception of data via radio signals. The device 700 additionally includes a power system 760, such as a battery, solar cell, fuel cell, or other system for generating, storing or providing power to the device. The power provided by the power system 760 is distributed as required to the various elements of the device 700.

In the description above, for the purposes of explanation, numerous specific details are set forth in order to provide a thorough understanding of the various embodiments. It will be apparent, however, to one skilled in the art that the embodiments described may be practiced without some of these specific details. In other instances, well-known structures and devices are shown in block diagram form. There may be intermediate structure between illustrated components. The components described or illustrated herein have additional inputs or outputs, which are not illustrated or described.

Various embodiments include processes performed by hardware components or embodied as machine-executable instructions that cause a general-purpose or special-purpose processor or logic circuits programmed with the instructions to perform the processes. The processes can also be performed by a combination of hardware and software. The machine-executable instructions reside on a computer-readable medium that is used to program the electronic device. The computer-readable medium may include, but is not limited to, floppy diskettes, optical disks, compact disk read-only memory (CD-ROM), and magneto-optical disks, read-only memory (ROM), random access memory (RAM), erasable programmable read-only memory (EPROM), electrically-erasable programmable read-only memory (EEPROM), magnet or optical cards, flash memory, or other type of computer-readable medium suitable for storing electronic instructions. Moreover, embodiments may also be downloaded as a computer program product, wherein the program may be transferred from a remote computer to a requesting computer.

If it is said that an element "A" is coupled to or with element "B," element A may be directly coupled to element B or be indirectly coupled through, for example, element C. When the specification or claims state that a component, feature, structure, process, or characteristic A "causes" a component, feature, structure, process, or characteristic B, it means that "A" is at least a partial cause of "B" but that there may also be at least one other component, feature, structure, process, or characteristic that assists in causing "B." If the specification or claim refers to "a" or "an" element, this does not mean there is only one of the described elements.

In one embodiment, a wearable device includes a set of low-power sensors that detect sensor input. The sensor input is transferred to processing logic that processes the sensor data provided by the low power sensors. The processing logic interprets the sensor data to detect a wake gesture used to wake a plurality of sub-systems of the wearable device from a low-power state. In one embodiment described herein, the set of low-power sensors includes a pressure sensor. The pressure sensor includes a low-power pressure-sensitive sensor element to generate pressure sensor data for a detected gesture.

In one embodiment, the wearable device additionally includes a low power proximity sensor that provides sensor data for a nudge wake gesture. The proximity sensor can provide gesture data that substitutes for pressure sensor data, or the proximity sensor can provide gesture data that is interpreted in conjunction with the pressure sensor data. In one embodiment, the wearable device additionally includes a light sensor that provides sensor data for a nudge wake gesture. The light sensor can provide gesture data that substitutes for pressure sensor data, or proximity sensor data, or the proximity sensor can provide gesture data that is interpreted in conjunction with the pressure sensor data, the proximity sensor data, or both the pressure sensor data and the proximity sensor data.

In one embodiment, the set of low-power sensors cause the device to wake a plurality of device sub-systems. The plurality of sub-systems can include a display device, to display status information. In one embodiment, the plurality of sub-systems includes an additional set of sensors, such as an accelerometer, a set of gyroscopes, a microphone, or a touch sensor. The additional sensors may have a higher power requirement than the low-power sensors used for wake nudge detection, and are maintained in a low-power state until awoken by wake gesture. The accelerometer and gyroscopes are used to detect motion and orientation of the wearable device and can be used to detect a command gesture, such as a lifting of the wearable device, followed by, or accompanied with a twist or turn of the display towards the user. The microphone is used to listen for voice commands. The touch sensor is used to accept touch input. The touch sensor can be integrated into the display of the wearable device, such as in a smartwatch face display, or otherwise integrated into a band or bracelet or the smartwatch device, to accept gesture command input in the form of a single touch, multiple consecutive touches, or multiple concurrent touches. In one embodiment, a short-range proximity sensor can substitute for a touch sensor.

In one embodiment, the set of low-power sensors used to detect the nudge gesture are also used to accept more advanced gestures and commands. After awakening, the additional sensors can be used in conjunction with more powerful sensor processing logic to accept nudge input commands which trigger specific device functionality. For example, a first nudge gesture can be used to wake the device, while a subsequent nudge gesture is interpreted as an input command (e.g., to enable one or more displays on the wearable device, to enable a voice input mode, to view a most recent notification, etc.). In one embodiment, multiple types of gestures are used to trigger specific device functionality. For example, a device can be configured to wake in response to a voice command that is detected in conjunction with pressure data.

In one embodiment, a system of electronic components comprises one or more displays, at least one of the displays including a touch sensitive region for touch input, where at least one of the one or more displays is in a low-power state. The system further includes processing logic coupled with the one or more displays, to process and interpret incoming sensor data from a set of sensors coupled to the processing logic. In one embodiment, the set of sensors includes a first sub-set of sensors in an active state and a second sub-set of sensors in an inactive state, where at least one sensor in the first sub-set of sensors is used to gather sensor data corresponding to a gesture, and wherein the gesture is used to cause the second sub-set of sensors to transition from an inactive to an active state. In one embodiment, the first sub-set of sensors includes a pressure sensor and the second sub-set of sensors includes an accelerometer. The pressure sensor and the accelerometer are each configured to detect sensor data for a gesture corresponding to a command executable by the processing logic. In one embodiment, the first sub-set of sensors further includes a proximity sensor or a light sensor and the second sub-set of sensors additionally includes a gyroscope. In one embodiment, a touch sensor is included in either the first or second sub-set of sensors.

In one embodiment, the set of sensors further includes a third sub-set of sensors in an inactive state, and wherein the second sub-set of sensors are used to gather data corresponding to a second gesture, wherein the second gesture is used to cause the third sub-set of sensors to enter an active state. In one embodiment, the second sub-set or third sub-set of sensors includes an infrared sensor to detect whether a user is looking at one of the one or more displays, or if one or more of the inactive displays is visible to the user, where an inactive display becomes active if visible to the user. The system described can be integrated into a wearable device. In one embodiment, the system is integrated into a smartwatch wearable device.

Many of the devices, systems and methods described herein are described in their most basic form, but processes can be added to or deleted from any of the methods, and components can be added to any of the devices or systems without departing from the basic scope of the embodiments. It will be apparent to those skilled in the art that many further modifications and adaptations can be made. Accordingly, the scope of the embodiments is not to be determined by the specific examples provided above but only by the claims below.

What is claimed is:

1. A system of electronic components comprising:
   one or more displays, at least one of the displays including a touch sensitive region for touch input, wherein at least one of the one or more displays supports a low-power state;
   processing logic coupled with the one or more displays, the processing logic to process and interpret sensor data to detect a gesture; and
   a set of sensors coupled to the processing logic, the set of sensors including:
   a first sub-set of sensors to operate in a normally active state, wherein the first sub-set of sensors includes a pressure sensor and at least one additional sensor to gather first sensor data for the processing logic, the first sensor data including at least pressure sensor data;
   a second sub-set of sensors to operate in a normally low-power state, the second sub-set of sensors including an accelerometer;
   wherein the processing logic is further to cause the second sub-set of sensors to enter an active state in response to detection of the gesture; and
   wherein the pressure sensor and the accelerometer are configured to gather second sensor data corresponding to a command executable by the processing logic.

2. The system of claim 1, wherein the at least one additional sensor in the first sub-set of sensors includes a proximity sensor or a light sensor.

3. The system of claim 1, wherein the second sub-set of sensors further includes a gyroscope.

4. The system of claim 1, wherein the first sub-set of sensors or the second sub-set of sensors includes at least one touch sensor.

5. The system of claim 1, wherein the set of sensors further includes a third sub-set of sensors to operate in the normally low-power state, and wherein the second sub-set of sensors gather data corresponding to a second gesture, wherein the second gesture is to cause the third sub-set of sensors to enter the active state.

6. The system of claim 5, wherein the second sub-set or third sub-set of sensors includes an infrared sensor.

7. The system of claim 6, wherein the infrared sensor is to detect sensor data indicating that one or more displays in a low power state is visible to a user, and wherein the one or more displays is enabled responsive to the indication.

8. The system of claim 1, wherein the system is integrated into a wearable device.

9. The system of claim 8, wherein the wearable device is a smartwatch.

10. A wearable device comprising:
    processing logic to process and interpret sensor data to detect a gesture; and
    a set of sensors coupled to the processing logic, the set of sensors including:

a first sub-set of sensors to operate in a normally active state, wherein the first sub-set of sensors includes a pressure sensor and at least one additional sensor to gather first sensor data for the processing logic, the first sensor data including at least pressure sensor data;

a second sub-set of sensors to operate in a normally low-power state, the second sub-set of sensors including an accelerometer, wherein the pressure sensor and the accelerometer are configured to gather second sensor data corresponding to a command executable by the processing logic.

11. The wearable device as in claim 10, wherein the processing logic is further to cause the second sub-set of sensors to enter an active state in response to detection of the gesture.

12. The wearable device as in claim 10, wherein the wearable device is a smartwatch device.

13. The wearable device as in claim 10, wherein the pressure sensor includes one or more force sensitive resistors.

14. The wearable device as in claim 10, wherein the processing logic processes the pressure sensor data via a trainable algorithm, the algorithm to detect that pressure continuously exceeds a threshold for greater than a period of time.

15. The wearable device as in claim 10 further comprising a light sensor, to generate light sensor data for the gesture, and wherein the processing logic is further to process the light sensor data detected by the light sensor to interpret the gesture.

16. The wearable device as in claim 10, additionally including a display device.

17. The wearable device as in claim 10, further comprising logic to cause the wearable device to enter a command input mode after waking from the low-power state, the command input mode to accept input commands and command gestures.

18. The wearable device as in claim 17, wherein the pressure sensor is to receive command gesture input for execution by the wearable device when the wearable device is in the command input mode.

19. A non-transitory machine-readable medium storing instructions to cause processing logic within a wearable device to perform operations, the operations comprising:
detecting a gesture by interpreting sensor data from a set of sensors coupled to the processing logic, the sensor data provided via a first sub-set of sensors configured to operate in a normally active state and a second sub-set of sensors configured to operate in a normally low-power state, the first sub-set of sensors including a pressure sensor and at least one additional sensor to gather first sensor data for the processing logic, the second sub-set of sensors including an accelerometer, and wherein the first sensor data includes at least pressure sensor data; and
gathering, via the pressure sensor and the accelerometer, second sensor data corresponding to a command executable by the processing logic.

20. The non-transitory machine-readable medium as in claim 19, the operations additionally comprising causing the second sub-set of sensors to enter an active state in response to detection of the gesture.

21. The non-transitory machine-readable medium as in claim 19, wherein interpreting sensor data from a set of sensors includes detecting, via the pressure sensor data, pressure continuously exceeding a threshold for greater than a period of time.

22. The non-transitory machine-readable medium as in claim 19, wherein interpreting sensor data from a set of sensors includes processing light sensor data detected by a light sensor to interpret the gesture.

23. The non-transitory machine-readable medium as in claim 19, the operations additionally comprising causing one or more displays to transition from a low power state in response to receiving the command executable by the processing logic.

24. The non-transitory machine-readable medium as in claim 19, further comprising instructions to perform additional operations including receiving accelerometer data from the accelerometer, the accelerometer data representing the command executable by the processing logic or a component of the gesture.

25. The non-transitory machine-readable medium as in claim 19, wherein the second sub-set of sensors includes a microphone and a touch sensor.

26. The non-transitory machine-readable medium as in claim 25, further comprising instructions to perform additional operations comprising receiving a voice command via the microphone.

27. The non-transitory machine-readable medium as in claim 25, further comprising instructions to perform additional operations including receiving touch sensor data from the touch sensor, the touch sensor data representing at least a portion of the command executable by the processing logic or a component of the gesture.

* * * * *